(12) United States Patent
Northrup

(10) Patent No.: US 8,053,214 B2
(45) Date of Patent: Nov. 8, 2011

(54) APPARATUS AND METHOD OF EXTRACTING AND OPTICALLY ANALYZING AN ANALYTE FROM A FLUID-BASED SAMPLE

(75) Inventor: Allen Northrup, Orinda, CA (US)

(73) Assignee: MicroFluidic Systems, Inc., Fremont, CA (US)

( * ) Notice: Subject to any disclaimer, the term of this patent is extended or adjusted under 35 U.S.C. 154(b) by 0 days.

(21) Appl. No.: 11/478,807

(22) Filed: Jun. 29, 2006

(65) Prior Publication Data
US 2006/0246501 A1 Nov. 2, 2006

Related U.S. Application Data

(63) Continuation of application No. 11/223,095, filed on Sep. 9, 2005.

(60) Provisional application No. 60/608,999, filed on Sep. 9, 2004.

(51) Int. Cl.
*C12P 19/34* (2006.01)

(52) U.S. Cl. ..................................... 435/91.2

(58) Field of Classification Search ............ 435/6, 283.1
See application file for complete search history.

(56) References Cited

U.S. PATENT DOCUMENTS

| | | | |
|---|---|---|---|
| 4,275,166 A | 6/1981 | McCollough et al. | 435/227 |
| 4,666,595 A | 5/1987 | Graham | 210/222 |
| 4,689,204 A | 8/1987 | Buck et al. | |
| 4,806,313 A | 2/1989 | Ebersole et al. | |
| 5,048,520 A | 9/1991 | Vago | 128/24 A |
| 5,475,203 A | 12/1995 | McGaffigan | 219/548 |
| 5,695,989 A | 12/1997 | Kalamasz | |
| 5,707,799 A | 1/1998 | Hansmann et al. | 435/6 |
| 5,812,272 A * | 9/1998 | King et al. | 506/39 |
| 5,952,173 A | 9/1999 | Hansmann et al. | 435/6 |
| 6,033,880 A | 3/2000 | Haff et al. | 435/91.1 |
| 6,087,183 A | 7/2000 | Zaromb | |
| 6,100,084 A | 8/2000 | Miles et al. | 435/306.1 |
| 6,136,555 A | 10/2000 | Jones | |
| 6,146,591 A | 11/2000 | Miller | 422/65 |
| 6,197,194 B1 | 3/2001 | Whitmore | |
| 6,228,634 B1 | 5/2001 | Blumenfeld et al. | 435/286.1 |
| 6,586,253 B1 | 7/2003 | Harrison et al. | |
| 6,692,968 B2 | 2/2004 | Burshteyn et al. | |
| 6,694,799 B2 | 2/2004 | Small | |
| 6,741,174 B2 | 5/2004 | Rhoades et al. | 340/540 |
| 6,905,885 B2 | 6/2005 | Colston et al. | 436/518 |
| 6,951,147 B2 | 10/2005 | Call et al. | 73/836.22 |
| 6,977,145 B2 | 12/2005 | Fouillet et al. | 435/6 |
| 7,005,982 B1 | 2/2006 | Frank | 340/539.26 |
| 7,006,923 B1 | 2/2006 | Rubin | 702/19 |
| 7,082,369 B1 | 7/2006 | Rubin et al. | 702/19 |
| 7,106,442 B2 | 9/2006 | Silcott et al. | 356/338 |
| 7,228,067 B2 | 6/2007 | Magni et al. | 392/480 |
| 7,329,388 B2 | 2/2008 | Guzman | |
| 7,713,232 B2 | 5/2010 | Uber, III et al. | |
| 2001/0032666 A1 * | 10/2001 | Jenson et al. | 136/256 |
| 2001/0036630 A1 * | 11/2001 | Ibrahim | 435/6 |
| 2002/0022261 A1 * | 2/2002 | Anderson et al. | 435/287.2 |
| 2002/0039783 A1 * | 4/2002 | McMillan et al. | 435/287.2 |
| 2002/0142482 A1 | 10/2002 | Wu et al. | 436/177 |
| 2002/0150933 A1 * | 10/2002 | Ehricht et al. | 435/287.2 |
| 2002/0151044 A1 | 10/2002 | Lemonnier | |
| 2002/0192114 A1 | 12/2002 | Lin et al. | |
| 2003/0038087 A1 | 2/2003 | Garvin | 210/767 |
| 2003/0073229 A1 | 4/2003 | Greenstein et al. | 435/287.2 |
| 2003/0215845 A1 | 11/2003 | Bille | 435/6 |
| 2004/0197793 A1 * | 10/2004 | Hassibi et al. | 435/6 |
| 2005/0064598 A1 | 3/2005 | Yuan et al. | 436/63 |
| 2005/0124073 A1 | 6/2005 | Freund | |
| 2005/0142565 A1 * | 6/2005 | Samper et al. | 435/6 |
| 2005/0227275 A1 * | 10/2005 | Jung et al. | 435/6 |
| 2006/0079000 A1 | 4/2006 | Floriano et al. | |
| 2006/0257853 A1 | 11/2006 | Herman | 435/5 |
| 2007/0116607 A1 | 5/2007 | Wang et al. | 422/83 |
| 2007/0248958 A1 | 10/2007 | Jovanovich et al. | |
| 2008/0050803 A1 | 2/2008 | Northrup et al. | 435/287.2 |
| 2008/0069733 A1 | 3/2008 | Maltezos et al. | |
| 2008/0125330 A1 * | 5/2008 | Cady et al. | 506/17 |

FOREIGN PATENT DOCUMENTS

| | | | |
|---|---|---|---|
| WO | WO 9612962 | * | 5/1996 |
| WO | WO 99/33559 A1 | | 7/1999 |
| WO | WO 03/070898 A2 | | 8/2003 |

OTHER PUBLICATIONS

"High Sensitivity PCR Assay in Plastic Micro Reactors", Jianing Yang et al., Physical Sciences Research Laboratories, Motorola Labs, Motorola, Inc., 7700 S. River Parkway, MD-ML34, Tempe, AZ 85284, USA, Revised Aug. 29, 2002, pp. 179-187.
International Search Report including the Written Opinion in reference to MFSI-01800WO. International Application No. PCT/US2009/62067, International Filing Date Oct. 26, 2009, Date of mailing Dec. 18, 2009, 9 pages.
Advisory Action, mail date Jul. 27, 2010, U.S. Appl. No. 11/223,095, filed Sep. 9, 2005, 3 pages.
Office Action for U.S. Appl. No. 11/223,095, filed Sep. 9, 2005, Mail date of office action is Sep. 14, 2010 and contains 13 pages.
Office Action dated May 26, 2009, U.S. Appl. No. 11/509,872, 10 pages.
Office Action mailed on Jul. 30, 2009, U.S. Appl. No. 11/510,073, filed Aug. 24, 2006, Allen Northrup, 11 pages.

* cited by examiner

Primary Examiner — Gary Benzion
Assistant Examiner — Cynthia Wilder
(74) Attorney, Agent, or Firm — Haverstock & Owens LLP

(57) ABSTRACT

An extraction and analysis device includes a microfluidic based collection system that extracts one or more different analytes from a fluid-based sample and an optical analysis system directly coupled to the collection system to perform optical analysis on the one or more collected analytes. The microfluidic based collection system includes microfluidic circuitry for directing a fluid based sample to a purification chip. Analytes collected within the purification chip can be either subsequently removed and analyzed or the analytes can be analyzed directly, while still within the purification chip, using the optical analysis system. The purification chip is preferably comprised of a plurality of pillars, the surface area of each pillar is coated with a specific capture chemistry. The specific capture chemistry is applied by derivitizing the pillars such that a ligand, such as a nucleic acid, an amptimer, or an antibody is attached to each pillar.

9 Claims, 9 Drawing Sheets

APPARATUS AND METHOD OF EXTRACTING AND OPTICALLY ANALYZING AN ANALYTE FROM A FLUID-BASED SAMPLE

RELATED APPLICATIONS

This Patent application is a continuation in part of U.S. patent application Ser. No. 11/223,095, filed Sep. 9, 2005, and entitled, "A Handheld and Portable Microfluidic Device to Automatically Prepare Nucleic Acids for Analysis", which claims priority of U.S. Provisional Patent Application Ser. No. 60/608,999, filed Sep. 9, 2004, and entitled "A Microfluidic System Using the Silicon Pillar Chip to Automatically Prepare DNA for Real-Time PCR Analysis", by the same inventors. This application incorporates U.S. patent application Ser. No. 11/223,095 and U.S. Provisional Application Ser. No. 60/608,999 in their entirety by reference.

FIELD OF THE INVENTION

The invention relates to a method and apparatus for collecting an analyte from a fluid-based sample and for performing an analysis on the collected analyte.

BACKGROUND OF THE INVENTION

Analytes, such as nucleic acids from a target organism, are typically part of a larger sample, with the rest of the material within the sample ranging from trace amounts to very abundant. These materials often interfere with or completely prevent detection of the organism and can make quantitative results impossible. Various extraction protocols and devices have been used to purify the sample, most of which are optimized for certain samples and applications.

Biological assays are particularly plagued with the added issue of the analyte's stability, viability, or even mutation, within the sample itself or sample purification methodology. Thus, for biological analysis, the challenges include two equally important and interacting factors: accuracy of the analytical method and efficiency of the sample purification for the analyte in the sample matrix. Since sample matrices are highly variable, a universal preparation protocol remains elusive.

The ability to process large volume liquid samples for PCR (polymerase chain reaction) based testing is ubiquitous to many different sample types. Water testing often demands analyses of sample volumes of tens to hundreds of milliliters to compensate for target dilution, with microbes, along with other particulates, typically concentrated into a smaller volume by a series of filtering and centrifugation steps. For air samples, particulates are captured either directly in collection fluid or on a filter and then eluted into a liquid. Soil samples involve suspending the soil in a liquid to release particulates from the soil colloids. Examples of large volume liquid samples include biological samples, such as blood for screening, or pharmaceutical samples for product validation. Samples are taken to a laboratory environment to perform analysis.

Fundamentally, collecting an analyte from within a sample relies on exploiting differences in physio-chemical properties between the background matrix and the analyte. In the case of nucleic acids, the polymer backbone provides a chain of negative charges at neutral pH. This feature is typically utilized as an adsorption target in most conventional techniques, including the combination of chaotropic agents and random surfaces of glass (packed beds of micro-beads, fibers, particles, etc.) in a plastic device in which the user flows a series of solutions, including the sample. Thus, conventional devices (e.g. Qiagen kits) based on this approach tend to have random surface interactions and flow characteristics. Performing an analysis of the analytes collected on such random surface is difficult if not impossible. As such, additional process steps are often necessary for removing and collecting the analyte from the random surface before an analysis can be performed.

Collecting analytes on a flat surface provides an advantage of being able to perform an analysis directly. However, the collection process on a flat surface is much less effective due to its two-dimensional nature. Not only does a flat surface provide reduced surface area over which to perform the collection, but the process is significantly slower. To collect an analyte on a flat surface requires letting the solution sit on top of the flat surface and through gravity or Brownian motion the analytes sink onto the surface. Such a process is slow and ineffective for high volumes.

SUMMARY OF THE INVENTION

The present invention is directed to an extraction and analysis device including a microfluidic based collection system that extracts one or more different analytes from a fluid-based sample and an optical analysis system directly coupled to the collection system to perform optical analysis on the one or more collected analytes. The microfluidic based collection system includes microfluidic circuitry for directing a fluid based sample to a purification chip. Analytes collected within the purification chip can be either be subsequently removed and analyzed or the analytes can be analyzed directly, while still within the purification chip, using the optical analysis system. The purification chip is preferably comprised of a plurality of protruding or raised structures, such as pillars, the surface area of each raised structure is coated with a specific or general capture chemistry or moiety. The capture chemistry is applied by derivitizing the raised structure so that an analyte, such as ligand, a nucleic acid, an antibody, an antigen, an amplifier, or an amptimer, is attached to each raised structure.

In one embodiment, a first antibody specifically binds to one particular analyte. In alternative embodiments, the first antibody comprises a plurality of different antibodies, each antibody specifically binding to one particular analyte. In such alternative embodiments, the plurality of antibodies can be used to collect a corresponding plurality of different analytes within a single purification chip. In another alternative embodiment, a capture chemistry applied to the plurality of raised structures comprises a DNA probe. A fluid-based sample flows past the raised structures and a DNA molecule hybridizes to the DNA probe.

Each purification chip is preferably modified to include a temperature control device coupled to the base of the purification chip, or a temperature control element included within, or on one or more surfaces of, the base of the purification chip, to thermally control a temperature of the raised structures and/or influence the temperature of any solution surrounding the raised structures. Such thermal control enables a multitude of thermally related process applications to be performed within the purification chip. One such application is performing PCR thermal cycling or isothermal cycling, either on the raised structures or in-solution surrounding the raised structures. Another such application takes advantage of the melt curves related to different numbers or types of DNA base pairs and enables the collection and analysis of multiple different DNA types within a given fluid-based sample.

DETAILED DESCRIPTION OF THE PRESENT INVENTION

Embodiments of an extraction and analysis device of the present invention are directed to a microfluidic based collection system that extracts one or more different analytes from a fluid-based sample and an optical analysis system directly coupled to the collection system to perform optical analysis on the one or more collected analytes. As used herein, "fluid" refers to either a gas or a liquid. The fluid-based sample can include a water-based fluid sample, a biological fluid sample, an environmental fluid sample, or any other fluid-based sample in which analytes are to be extracted. An analyte is preferably a biological entity, such as a nucleic acid. Alternatively, an analyte is an amino assay, including but not limited to proteins, molecules, or whole cells. Still alternatively, an analyte is any substance that can be collected from a fluid-based sample and subject to a detection and analysis. The microfluidic based collection system includes microfluidic circuitry for directing a fluid based sample to a purification chip. The fluid based sample is forced through the purification chip at a controlled flow rate. Analytes collected within the purification chip can be either be subsequently removed and analyzed or the analytes can be analyzed directly, while still within the purification chip, using the optical analysis system.

Figure 1:
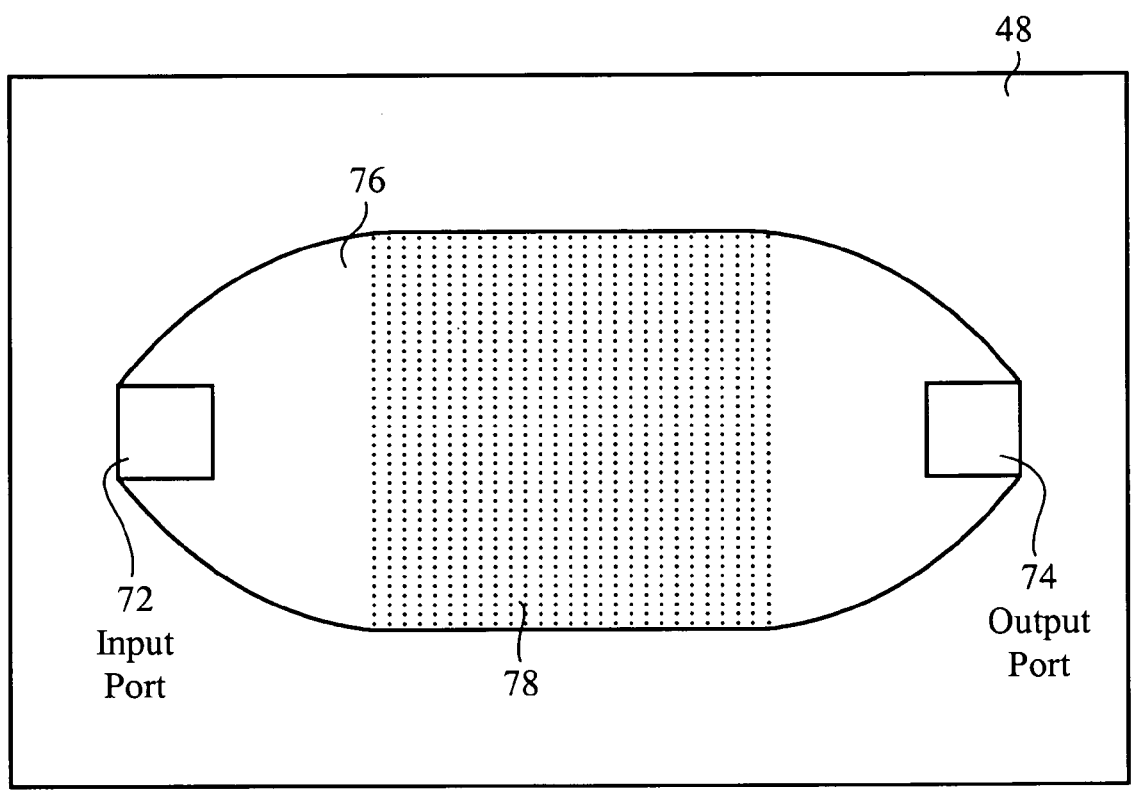
FIG. 1 illustrates a top down view of the purification chip.

The purification chip is preferably of the type described in U.S. Pat. Nos. 5,952,173 and 5,707,799, the entirety of which are both hereby incorporated by reference. FIG. 1 illustrates a top down view of a purification chip 48 used in the extraction and analysis device of the present invention. The purification chip 48 includes a fluid chamber 76. The fluid chamber 6 includes an input port 72, a plurality of raised structures 78, and an output port 74. Preferably, the raised structures are configured as pillars. Fluid-based sample flows into the fluid chamber 76 via the input port 72. The fluid chamber 76 is preferably tear drop shaped such that fluid-based sample entering the fluid chamber 76 disperses outward to interface with the plurality of pillars 78. In the preferred embodiment, the plurality of pillars 78 are uniformly positioned within the fluid chamber 76. Alternatively, the pillars 78 can be arranged in any desired geometrical configuration. Preferably, the pillars 78 are arranged in columns, each column substantially perpendicular to a fluid flow path from the input port 72 to the output port 74. The position of the pillars 78 in each column are preferably staggered between adjacent columns to prevent row alignment of the pillars 78.

A specific capture chemistry is applied to each of the pillars 78. The specific capture chemistry is applied by derivitizing the pillars 78 such that a first antibody is attached to each pillar 78. In one embodiment, the first antibody specifically binds to one particular analyte. In alternative embodiments, the first antibody comprises a plurality of different antibodies, each antibody specifically binding to one particular analyte. In such alternative embodiments, the plurality of antibodies can be used to collect a corresponding plurality of different analytes within a single purification chip.

A derivitized surface area of each of the pillars 78 contacts the fluid-based sample as it flows past. As the fluid-based sample makes contact with the pillar 78, the analyte binds to the antibody attached to the pillars 78. Exemplary methods of performing such a collection process are described in U.S. Pat. Nos. 5,952,173 and 5,707,799.

In an alternative embodiment, a capture chemistry applied to the plurality of pillars comprises a nucleic acid probe. A fluid-based sample flows past the pillars and a nucleic acid molecule hybridizes to the nucleic acid probe. The nucleic acid probe is specific for a nucleic acid sequence. In this alternative embodiment, the pillars are used to bind specific nucleic acid molecules. In yet another alternative embodiment, the pillars within a given purification chip are configured with a multitude of different capture chemistries used to bind a corresponding number of different moieties. For example, the pillars for a single purification chip are configured to capture both one or more analytes and one or more specific nucleic acid molecules.

Single crystal silicon, used routinely in the semiconductor industry, can be formed using the same type of equipment and processes to create micron and sub-micron structures such as found in conventional MEMS (micro-electro-mechanical systems) devices. As applied to the purification chip of the present invention, the surfaces of the pillars 78 are chemically modified to exploit the physio-chemical differences between the analyte and the fluid-based sample, and since the structure size and shape of the pillars can be designed, the microfluidic aspects are also modified and controlled to enhance extraction. The combination of micro-structured surfaces with microfluidic properties that are designed and tested allows for new sample purification devices which are used in a variety of applications, such as extraction and concentration of nucleic acids, amino assays, or other analytes. The glass-surface nature of the oxidized single crystal silicon structures lends itself to the application of the silicon oxide-mediated binding methods to adsorb nucleic acids.

The purification chip used within the extraction and analysis device of the present invention is preferably designed to exploit the benefits of silicon structures for analyte extraction, purification and concentration. The properties of the purification chip including flow-through characteristics, high-surface area, and low-fluid volume allow for processing large sample volumes and reducing the extracted analytes into very small volumes, act to yield high concentration effects.

In the preferred embodiment, each purification chip of the present invention is modified to include a temperature control device coupled to the base of the purification chip, such as a temperature control element included within the base of the purification chip, to thermally control a temperature of the pillars and/or influence the temperature of any solution surrounding the pillars. The temperature control device can include a resistive heater, an optical heater, an infrared heat, a thin film heater, or any other conventional heating and/or cooling means. Applications that accumulate analytes on the pillars can use such thermal control to heat or cool the analytes or binding chemistries directly through their attachment to the pillars. Applications that require heating or cooling of a solution surrounding the pillars can use the thermal control to heat or cool the solution through contact with the pillars. Where temperature control is critical for certain process steps, or where the rate of a particular process step can be increased with proper temperature control, the thermal control of the pillars provided by the present invention is advantageous.

Figure 2:
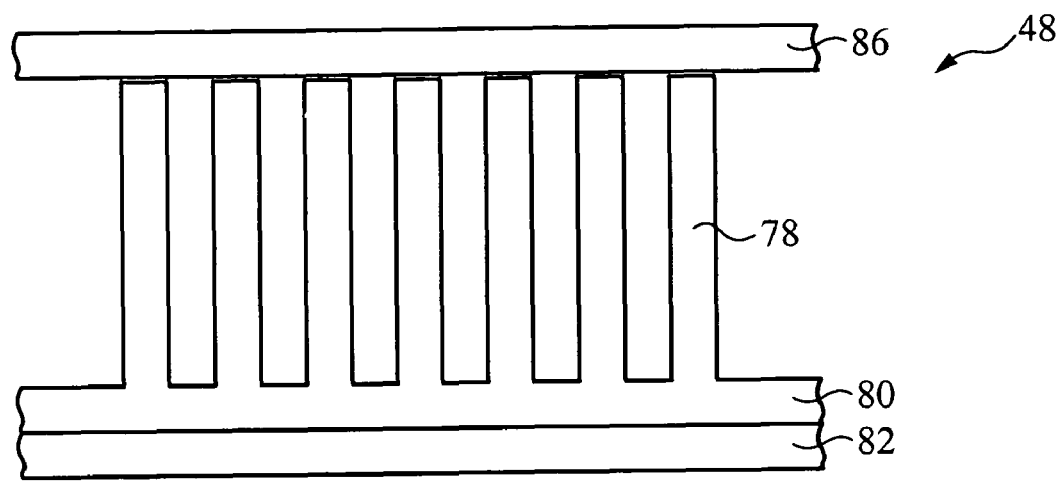
FIG. 2 illustrates a side view of the purification chip of FIG. 1 in which a temperature control element is coupled to the base of the purification chip.

FIG. 2 illustrates a side view of the purification chip 48 of FIG. 1. The purification chip 48 is modified such that a temperature control device 82 is coupled to a base 80 of the purification chip 48. A thermally conductive interface is formed between the temperature control device 82 and the base 80 such that heat is transferred between the temperature control device 82 and the base 80. The temperature control device 82 is preferably coupled to a power source (not shown) and a control (not shown) that enables a temperature of the temperature control device 82 to be controlled up, down, or constant. The pillars 78 and the base 80 are preferably comprised of a heat conducting material, such as silicon. Heat is transferred between the temperature control device 82 and the base 80, and thereby to the pillars 78, such that a temperature of the pillars 78 is controlled by controlling the temperature of the temperature control device 82. The temperature of the pillars 78 is adjusted by adjusting the temperature of the temperature control device 82. A cover 86 hermetically seals the fluid chamber 76 (FIG. 1). Preferably, the cover 86 is optically transparent.

Figure 3:
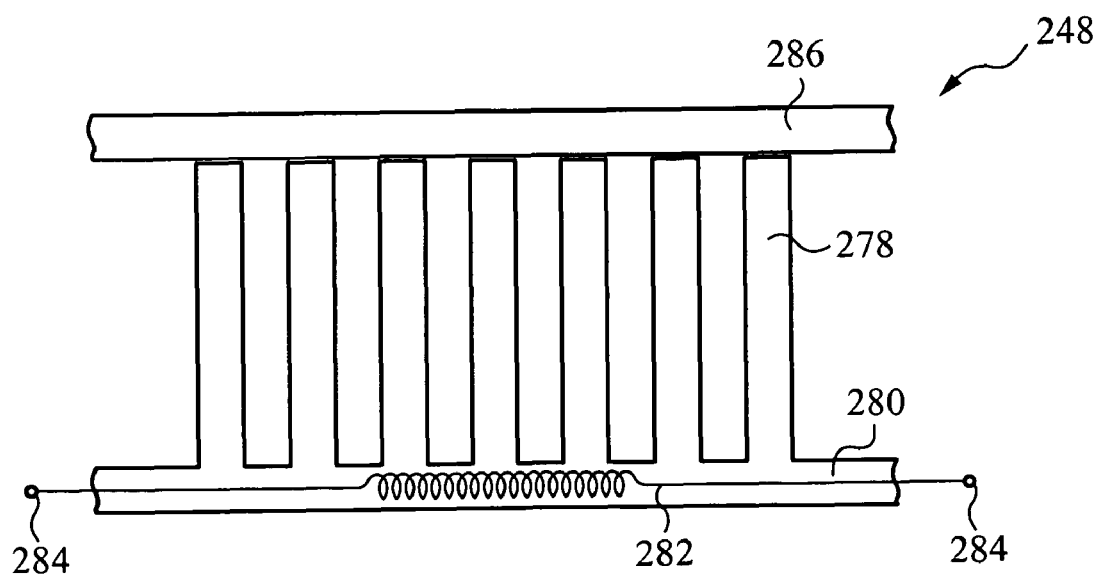
FIG. 3 illustrates a side view of an alternative embodiment of a purification chip in which a temperature control element is configured within the base of the purification chip.

FIG. 3 illustrates a side view of an alternative embodiment of a purification chip in which a temperature control device is configured within a base of the purification chip. A purification chip 248 is configured similarly to the purification chip 48 with the exception that a base 280 of the purification chip 248 is modified to include an integrated temperature control device 282. The temperature control device 282 includes electrical contacts 284. The electrical contacts 284 are coupled to a power source (not shown) and a control (not shown) that enables a temperature of the temperature control device 282 to be controlled up, down, or constant. The pillars 278 and the base 280 are comprised of heat conducting material, such as silicon. Similar to the function of the temperature control device 82 related to the purification chip 48 in FIG. 2, the embedded temperature control device 282 is controlled to regulate a temperature of the pillars 278 within the purification chip 248. A cover 286 hermetically seals a fluid chamber of the purification chip 248. The cover 286 is optically transparent.

As described above, a fluid-based sample flows through the purification chip 48 such that one or more analytes are accumulated on the pillars 78. To receive the fluid-based sample, the purification chip 48 is preferably coupled to a cartridge that includes microfluidic circuitry for providing the fluid-based sample to the purification chip 48 and for receiving the fluid-based sample after passing through the purification chip 48. The microfluidic circuitry is configured with one or more pathways such that one or more fluids, including, but not limited to, the fluid-based sample, washing and rinsing fluids, different types of reagents and chemicals for multi-step processes, and different types of antibodies, are provided to the purification chip 48.

The extraction and analysis device of the present invention is also directed to detecting and analyzing the one or more accumulated analytes while still bound to the pillars within the purification chip. The extraction and analysis device includes a detection and analysis system coupled to the purification chip to perform the optical analysis. In the preferred embodiment, optical detection is performed using an optical analysis system.

Most analytes need to be prepared before the optical analysis system is capable of detecting them. One method of preparing the analyte is to flow a second antibody through the purification chip, where the second antibody is characterized by its ability to bind with a specific analyte accumulated on the pillars. In the case where more than one analyte is accumulated on the pillars, a separate second antibody for each analyte, with corresponding binding characteristics for each analyte, is delivered through the purification chip. Each of the analyte-specific second antibodies can be delivered in succession, or mixed together according to various combinations. Included on the second antibody is an enzyme, marker, flourescent tag, or any other conventional mechanism that generates a measurable characteristic. Where more than one analyte is to be detected, the marker for each separate second antibody must be distinct from one another such that each individual analyte is uniquely detectable. After the second antibody is attached to the analyte, a third fluid is directed into and held in the fluid chamber of the purification chip. The third fluid acts to induce a signal attached to the second antibody. The signal moiety floats in the third solution surrounding the pillars and acts as a measurable signal that the optical analysis system can detect. Alternatively, a third fluid is not utilized and the marker is detected by the optical analysis system while still attached to the second antibody.

A similar method is used to prepare captured nucleic acid molecules for detection. A detectable substance, such as a flourescent signal, is generated which indicates the presence of a specific nucleic acid molecule type. The detectable substance can either be generated in solution or directly on the nucleic acid molecule attached to the pillars. It is understood that other conventional methods for detecting nucleic acid molecules can be utilized.

Using the extraction and analysis system of the present invention, very rapid detection processes are performed in which the presence of a substance is detected in a relatively short period of time. For example, the previously described method in which a first solution, the fluid-based sample, is passed through the purification chip to accumulate an analyte, then a second solution that includes the second antibody is passed through the purification chip, then a third solution that dislodges the marker from the second antibody is directed into the purification chip, and finally an optical analysis is performed on the marker, while the third solution is still in the purification chip, to obtain picomolar detection of the analyte is performed in three to four minutes. In the preceding example, each of the first solution, the second solution, and the third solution flow through the chip at a rate of approximately 2-3 ml per minute.

As described above, the pillars within the purification chip are thermally controlled. Such thermal control enables the inclusion of any temperature sensitive processing steps necessary to accumulate analytes on the pillars and/or in-solution between the pillars. Additionally, any temperature sensitive processing steps necessary to perform subsequent optical detection steps can also be performed.

Thermal control of the pillars enables additional functionality. One such function is to perform PCR (polymerase chain reaction) on the surface of the pillar, or within the solution surrounding the pillars, by successively heating and cooling the pillars. Depending on the thermal characteristics of the substance bound to the pillar, heating the pillars to a substance-specific temperature essentially melts, or breaks, the binding between the substance and the derivatized pillar. Cooling the pillars enables the substance to once again bind to the derivatized pillar. In this manner, a thermal cycling PCR reaction is enabled by thermally controlling the pillars. The pillars themselves also function as effective heaters such that even if PCR is not being performed on the surface of the pillars, heating the pillars enables thermal control of the surrounding solution through which a reaction can occur in-solution.

In a specific application, different length nucleic acid probes are attached to the pillars. For example, attached to the pillars are nucleic acid probes with five bases and nucleic acid probes with seven bases. A first type of nucleic acid molecule binds with the five-base nucleic acid probe and a second type of nucleic acid molecule binds with the seven-base nucleic acid probe. Melt curves are well known in the art. Melt curves generally indicate that the more base pairs that bind a nucleic acid probe and a nucleic acid molecule, the greater the temperature required to melt the binding. As such, the binding between the first type of nucleic acid molecule and the five-base nucleic acid probe is melted at a lower temperature than the binding between the second type of nucleic acid molecule and the seven-base nucleic acid probe. By controlling the temperature of the pillars, the first type of nucleic acid molecule is removed, by melting, from the pillars while the second type of nucleic acid molecule remains bound to the pillars. The solution containing the removed first type of nucleic acid molecule is subsequently flushed from the purification chip as waste or collected for analysis or other use. The second type of nucleic acid molecule that remains bound to the pillars can then be analyzed directly within the purification chip, or a subsequent melting step is performed by further raising the temperature of the pillars to melt the second type of nucleic acid molecule from the seven-base nucleic acid probe. It is understood that a similar process can be used to accumulate and remove more than two different types of nucleic acid molecules.

Although the above application describes the accumulation and staggered melting off of different types of nucleic acid molecules, thermal control of the pillars enables a similar process to be performed related to any type of analyte, or other accumulated substance on the pillars, that can be removed from the pillars at distinct temperatures.

Thermally controlling the pillars also enables the synthesis of nucleic acid. In one such application, nucleic acid is synthesized within a solution surrounding the pillars. As is well known in the art, a double stranded nucleic acid can be synthesized from a single-stranded nucleic acid by adding a primer, which is essentially the same as a nucleic acid probe, which binds to a specific sequence of the single-stranded nucleic acid. An enzyme is then applied whereby additional bases are added to the primer that match the bases on the single-stranded nucleic acid. In essence the single-stranded nucleic acid functions as a template. By heating the pillars to the proper temperature, the double-stranded nucleic acid is split into two separate single-stranded nucleic acid, both of which can be subsequently used as templates during a next round of nucleic acid synthesis.

A similar process is also performed where the nucleic acid probe is attached to the pillars. A corresponding single-stranded nucleic acid binds to the nucleic acid probe. The attached single-stranded nucleic acid then functions as a template whereby a double-stranded nucleic acid is formed attached to the pillars. The pillars are heated to a temperature at which the double-stranded nucleic acid splits, leaving one single-stranded nucleic acid still attached to the pillar and the other single-stranded nucleic acid floating in solution. There exist flourescent probes that light up in the presence of double-stranded nucleic acid. So before the melting step is performed, the flourescent probes can be added to detect the presence of double-stranded nucleic acid. Very specific nucleic acid detection can be performed in this manner.

Figure 4:
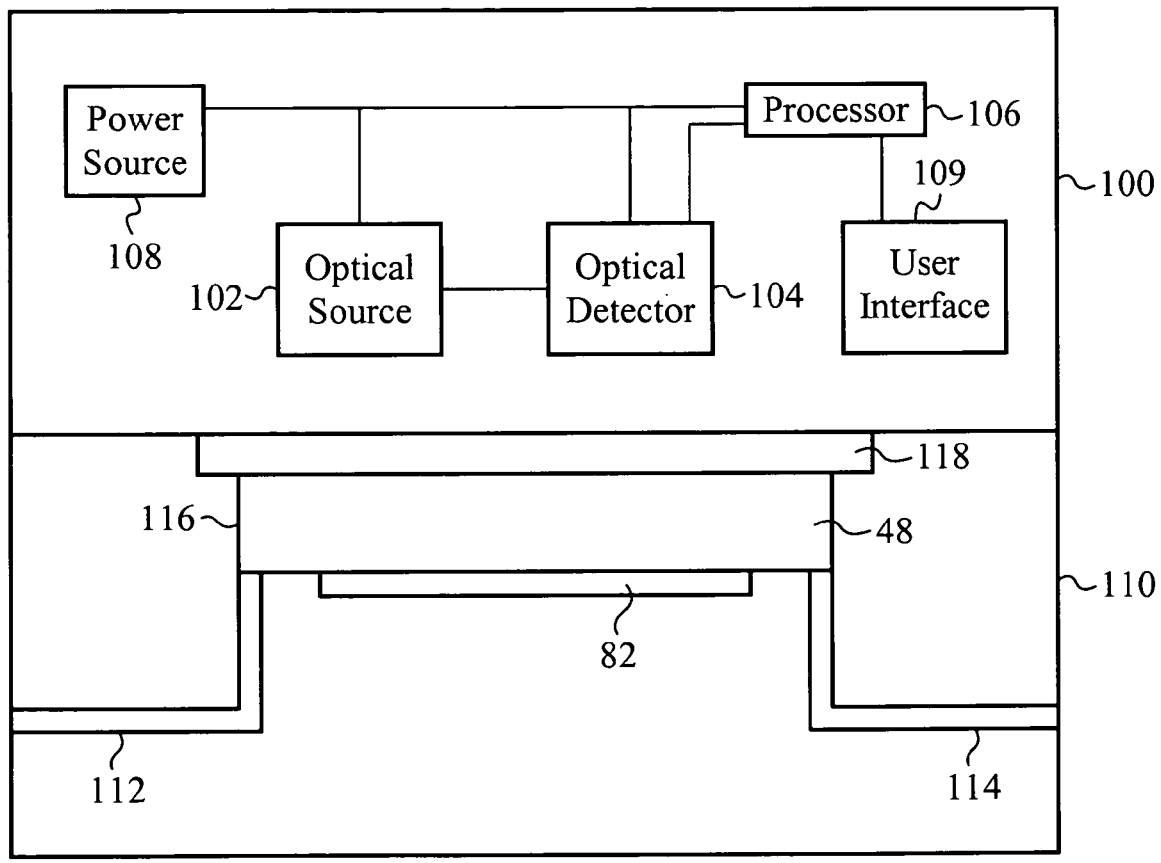
FIG. 4 illustrates a single chip system in which the purification chip is mounted within a cartridge and coupled to an optical analysis system.

FIG. 4 illustrates an exemplary single chip system in which the purification chip 48 is mounted within a cartridge 110 and coupled to an optical analysis system 100. The cartridge 110 includes a chip holder 116 into which the purification chip 48 is placed. The cartridge 110 also includes inlet microfluidic circuitry 112 to provide fluid to the inlet port 72 (FIG. 1) and outlet microfluidic circuitry 114 receive fluid from the outlet port 74 (FIG. 1). The purification chip 48 is covered and secured into the chip holder 116 with a cover 118. The optical analysis system 100 is coupled to the purification chip 48. In one embodiment, the cover 118 is optically transparent such that the optical analysis system 100 is coupled to the cover 118 to perform optical analysis on collected analyte within the purification chip 48. In another embodiment, the cover 118 is removed, and the optical analysis system 100 is coupled to the optically transparent cover 86 (FIG. 2) of the purification chip 48 to perform optical analysis. In an alternative embodiment, the cartridge 110 includes one or more solution containers which store the solutions necessary to perform the optical analysis, such as an antibody and/or an enzyme.

The optical analysis system includes an optical source 102, and optical detector 104, a processor 106, a power source 108, and a user interface 109. The power source 108 is either self-contained, such as a battery, or the power source 108 is supplied electrical current from an external electrical outlet. The optical source 102 directs light into the fluid chamber 76 (FIG. 1) of the purification chip 48. The optical source 102 can be configured to provide any wavelength of light necessary to perform the required optical analysis. The optical source 102 is any conventional light source including, but not limited, to an LED or a laser light provided via fiber optics. The optical detector 104 is any conventional optical detection device capable of detecting light directed from the purification chip 48 in response to the optical source 102. The processor 106 controls operation of the optical source 102 and optical detector 104, performs analysis of the measurements received from the optical detector 104, and provides results of the analysis to the user interface 109. In general, the optical analysis system is configured to perform an optical detection method such as a fluorescence method, a time resolved fluorescence method, or a chemical-luminescence method. The user interface 109 preferably includes a keypad to enable a user to provide instructions to the processor 108 and a display to provide instructions and to display the results of the analysis performed by the processor 108.

Figure 5:
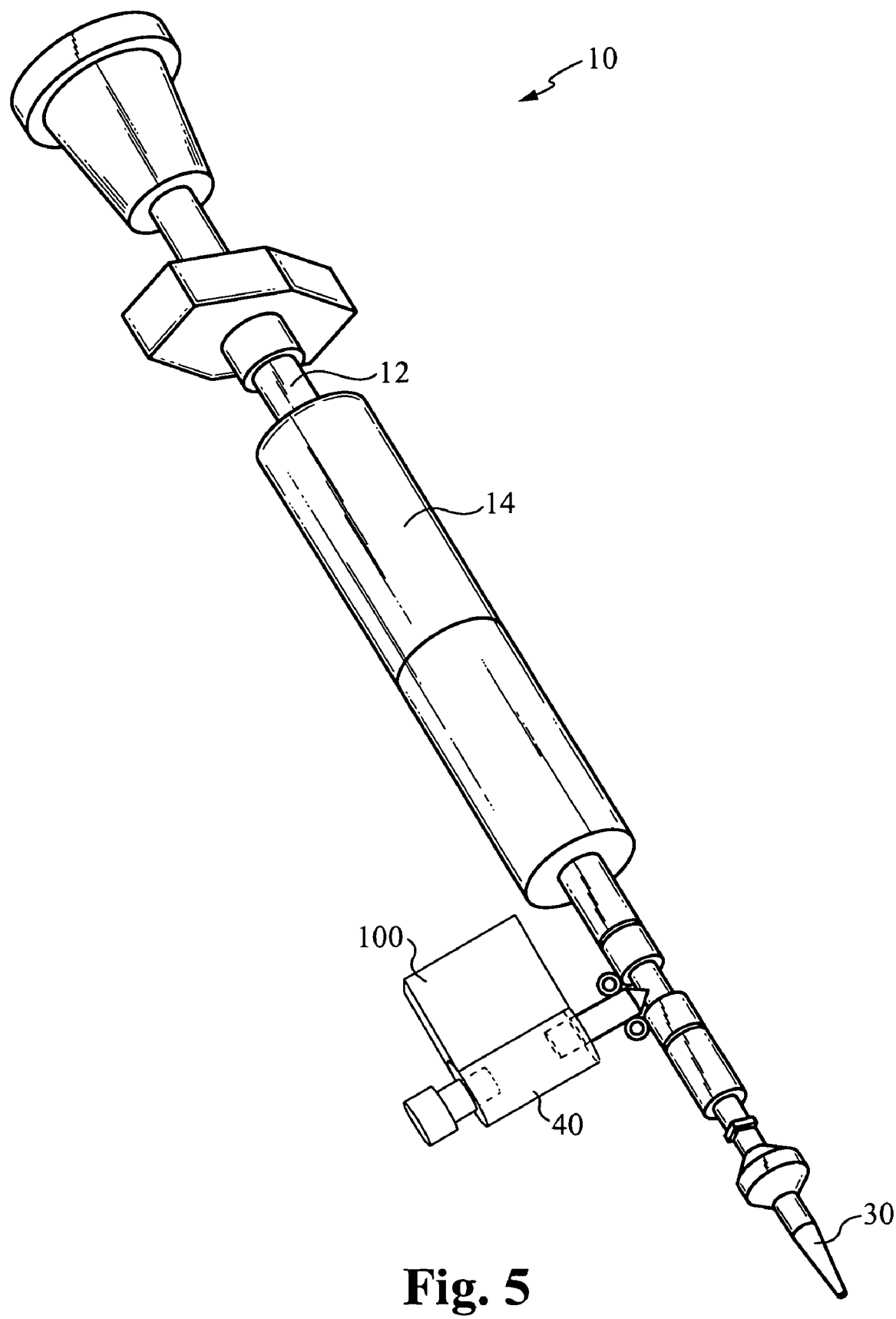
FIG. 5 illustrates a perspective view of a handheld and portable extraction device utilizing the single chip system.

An exemplary application of the single chip system is a handled and portable extraction device. FIG. 5 illustrates a perspective view of a handheld and portable extraction device 10 that utilizes the single chip system. The extraction device 10 includes a plunger 12 configured within a syringe barrel 14. The plunger 12 moves in and out of the syringe barrel 14. The syringe barrel 14 is coupled to a pipette tip 30. A chip block 40 is coupled to the syringe barrel 14. The optical analysis system 100 is coupled to the chip block 40. Preferably, the optical analysis system 100 is configured to be de-coupled from the chip block 40. Alternatively, the chip block 40 and the optical analysis system 100 form an integrated component.

Figure 6:
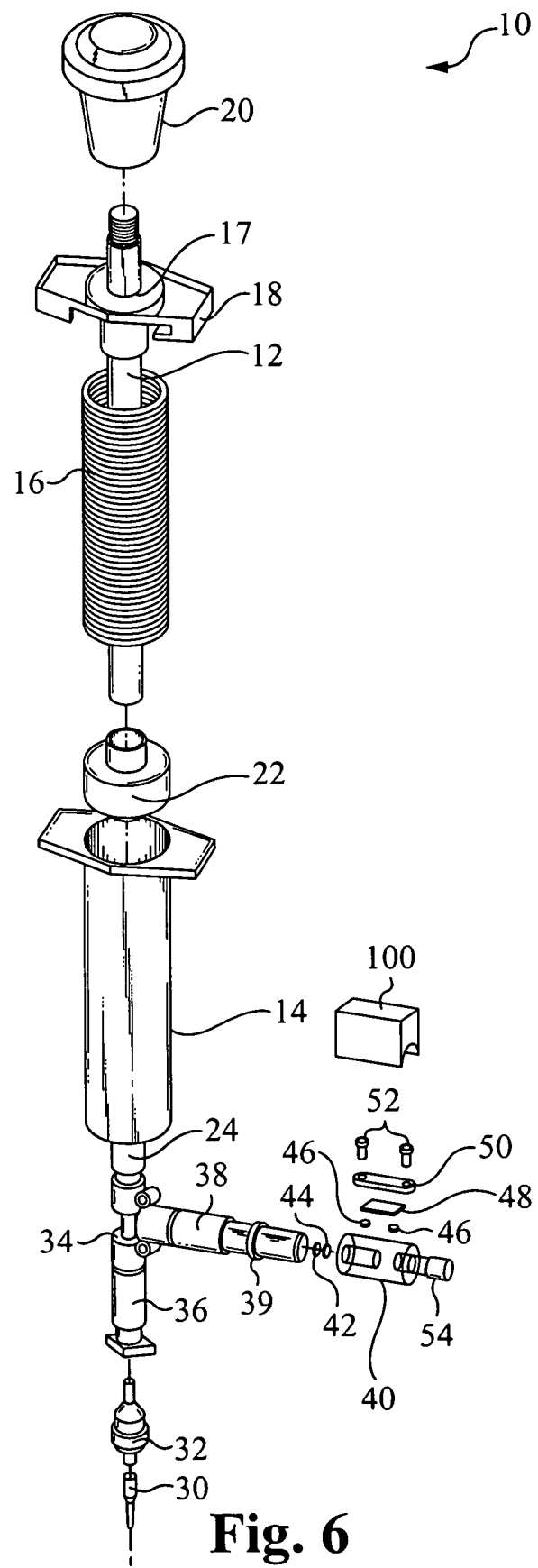
FIG. 6 illustrates an exploded view of the handheld and portable extraction device of FIG. 5.

FIG. 6 illustrates an exploded view of the extraction device 10. The plunger 12 includes a handle 18, a cap 20, and a plunger seal 22. The plunger seal 22 provides a seal between fluid collected in a lower portion of the syringe barrel 14 and an upper portion of the syringe barrel that contains the plunger 12. The handle 18 is secured to the syringe barrel 14. The handle 18 is secured by a twist lock mechanism as shown. The plunger 12 fits through a central aperture 17 within the handle 18 such that the plunger 12 can move in and out of the syringe barrel 14 while the handle 18 remains secured in place. A spring 16 is coupled to the plunger 12 to bias the plunger 12 inward.

The plunger 12 is moved out of the syringe barrel 14 by manually pulling on the cap 20. Outward movement of the plunger 12 increases a spring compression in the spring 16. Once the cap 20 is released, the spring 16 releases its spring compression thereby forcing the plunger 12 downward through the spring barrel 14.

The syringe barrel 14 also includes a fluid port 24 through which a fluid is aspirated into the syringe barrel 14 upon outward movement of the plunger 12. The fluid port 24 is coupled to a tee junction 34. The tee junction 34 is coupled to an input check valve 36 and an output check valve 38. The input check valve 36 is coupled to a filter holder 32. The filter holder 32 includes a membrane filter (not shown) to separate physical debris from an incoming fluid-based sample. Alternatively, the filter holder 32 includes any type of separating means to separate physical debris from fluid-based sample passing therethrough. The filter holder 32 is coupled to a pipette tip 30.

The output check valve 38 is coupled to the chip block 40 via a threaded nipple 39. The threaded nipple 39 holds an o-ring 42 and a filter 44 against the chip block 40. The filter 44 is a membrane filter similar to the membrane filter included within the filter holder 32. Alternatively, the filter 44 is a frit or any other type of separating means capable of separating physical debris from a fluid-based sample. Although the extraction device 10 is configured to include two filters, a first filter within the filter holder 32 and the second filter 44, it is understood that more, or less, filters can be included within the extraction device 10 to separate physical debris from a fluid-based sample. The chip block 40 is coupled to a waste collector (not shown) via waste connector 54.

Figure 7:
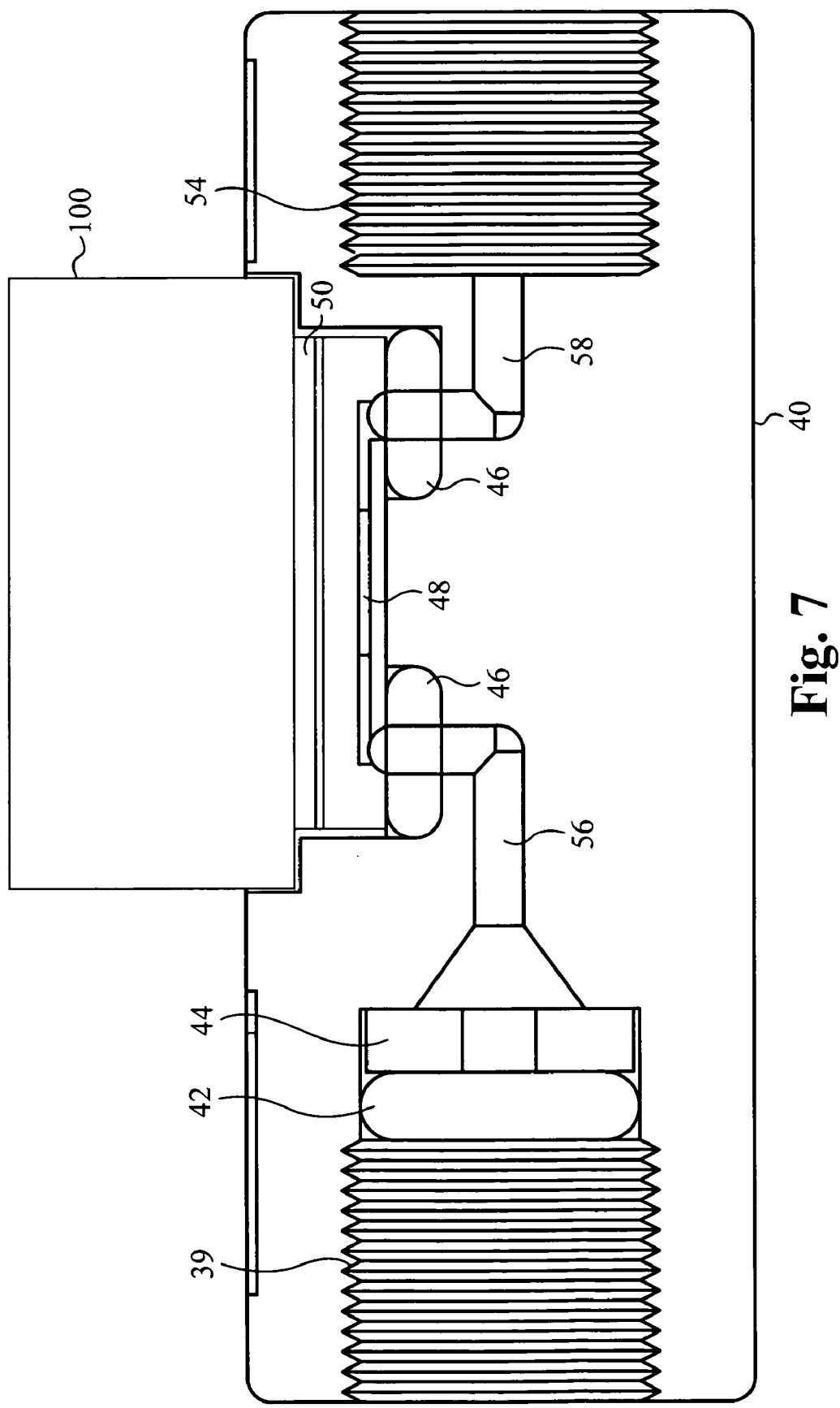
FIG. 7 illustrates a cut-out side view of the chip block and optical analysis system in FIG. 5.

The chip block 40 includes the purification chip 48, o-rings 46, a block plate 50, and block plate screws 52, as illustrated in the exploded view in FIG. 6 and also as illustrated in a cut-out side view in FIG. 7. As shown in FIG. 7, the threaded nipple 39 fits within the chip block 40 and against the o-ring 42. The o-ring 42 fits against the filter 44. A microfluidic circuit 56 is coupled to the filter 44 and to an input port of the purification chip 48. A microfluidic circuit 58 is coupled to an output port of the purification chip 48 and the waste connection 54. The waste connection 54 fits within the chip block 40. An o-ring 46 seals the microfluidic circuit 56 to the input port of the purification chip 48, and another o-ring 46 seals the microfluidic circuit 58 to the output port of the purification chip 48.

The purification chip 48 is removable from the chip block 40. The block plate 50 secures the purification chip 48 in position within the chip block 40. The block plate 50 is secured to the chip block 40 using block plate screws 52 (FIG. 6). The block plate 50 is optically transparent. The optical analysis system 100 is coupled to the block plate 50.

Figure 8:
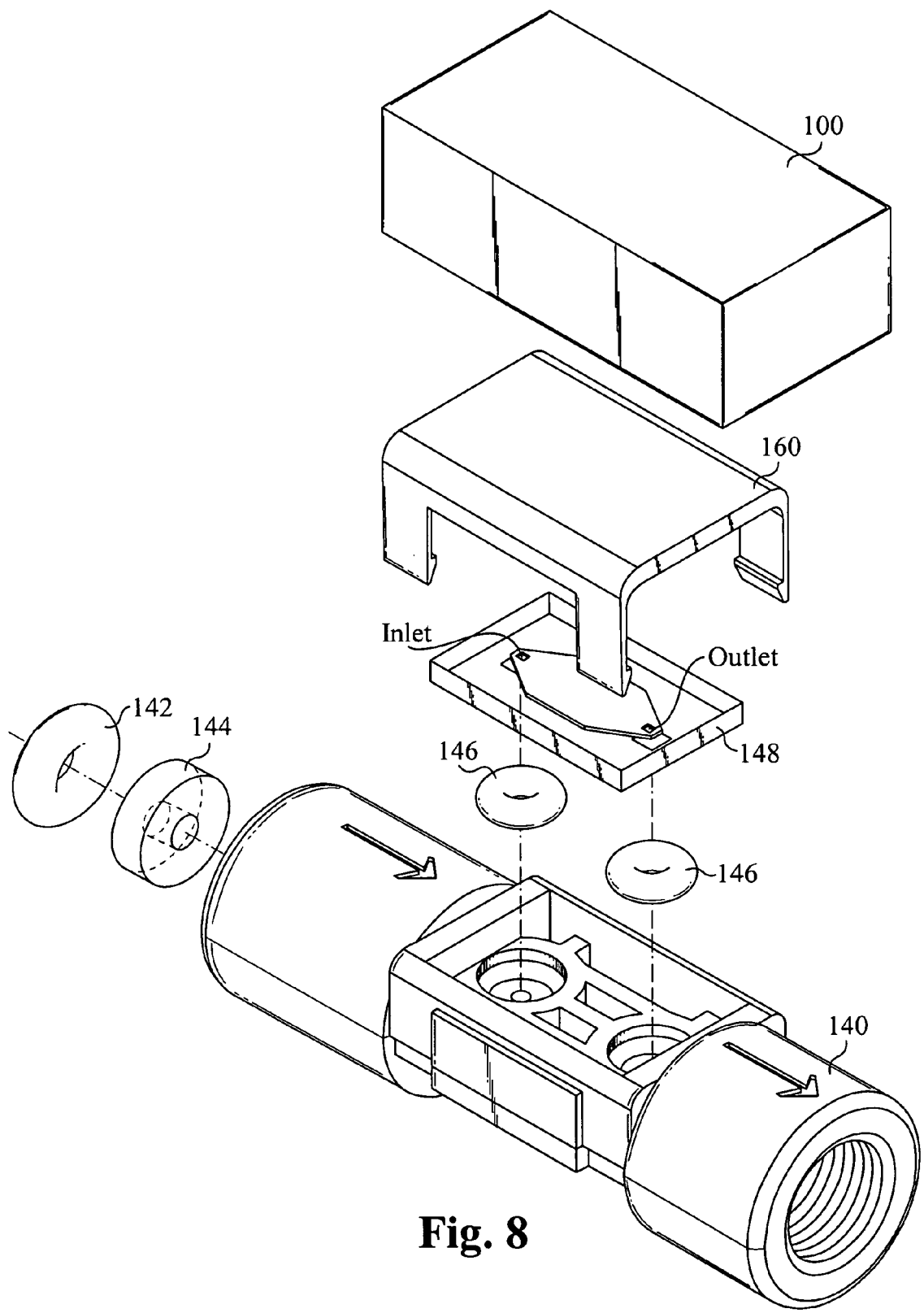
FIG. 8 illustrates an exploded view of an alternative chip block assembly.

FIG. 8 illustrates an alternative embodiment of a chip block 140. The alternative chip block 140 is a molded block configured to receive the output connection threaded nipple 39 (FIG. 6) and the waste connection 54 (FIG. 6). The chip block 140 includes an o-ring 142 and a frit 144 to couple the threaded nipple 39 to the chip block 140. O-rings 146 seal a purification chip 148 to the chip block 140. A cap 160 fits over the purification chip 148 and secures to the body of the chip block 140. The cap 160 and the purification chip 148 are removable. The cap 160 is optically transparent. The optical analysis system 100 is coupled to the cap 160. Flow of the fluid-based sample through the chip block 140, including collection of one or more analytes within the purification chip 148, is similar to that described above in relation to the preferred chip block 40 and purification chip 48. The optical analysis system 100 performs optical analysis on the one or more analytes collected within the purification chip 148. The optical analysis is performed through the optically transparent cover 160. Alternatively, the cap 160 is removed and the optical analysis system 100 is coupled directly to the purification chip 148 to perform the optical analysis. In this alternative embodiment, the cover 160 does not need to be optically transparent.

Referring to FIG. 6, the spring 16 of the handheld and portable extraction device 10 is selected such that the spring compression and associated force applied to the fluid-based sample collected within the syringe barrel 14 generates a desired fluid flow rate of the fluid-based sample as it passes the plurality of pillars 78 within the purification chip 48. In an alternative embodiment, the spring 16 is replaced with an alternative means for producing the desired fluid flow rate. For example, air pressure using a $CO_2$ cartridge, a hand pump, or an electrical actuation means such as a motorized screw, is used to apply inward force on the plunger. The potential energy of the applied force is generated either after the fluid-based sample is drawn into the syringe barrel, or generated as the plunger is pulled outward of the syringe barrel to draw in the fluid-based sample. The means for producing the desired fluid flow rate can either be automated or manual. The plurality of pillars 78 collect one or more analytes from the fluid-based sample at peak efficiency based on a select fluid flow rate. Optimum fluid flow rates are determined by experimentation and are dependent on the type of analyte to be collected, the density of the plurality of pillars, the surface composition of the plurality of pillars, the composition of the fluid-based sample, and the like.

Operation of the extraction device 10 is described in relation to FIGS. 1, 6, and 7. The pipette tip 30 is placed within a fluid-based sample. The plunger 12 starts in a down position where the plunger seal 22 is positioned at the bottom of the syringe barrel 14 against the fluid port 24. To draw the fluid-based sample into the extraction device 10, the plunger 12 is moved outwardly within the syringe barrel 14 by pulling on the cap 20. Outward movement of the plunger 12 aspirates fluid-based sample into the pipette tip 30 through the filter holder 32 to the input check valve 36. As the plunger 12 is pulled outwardly of the syringe barrel 14, the check valve 36 directs the input fluid-based sample from the input check valve 36 to the fluid port 24. The fluid-based sample flows through the fluid port 24 and into the syringe barrel 14. As the plunger 12 is pulled outward, the output connection check valve 38 prevents any backflow of fluid or air through the output path.

As the plunger 12 is pulled outward, spring compression in the spring 16 increases. The plunger 12 is pulled outward until the spring 16 prevents any further outward movement. At this maximum outward position, a maximum spring compression is substantially reached. Alternatively, the plunger 12 is pulled outward to a position that is less than the maximum outward position such that the plunger 12 remains within the syringe barrel 14.

The cap 20 is then released, whereby the spring 16 forces the plunger 12 into the syringe barrel 14. As the plunger 12 moves downward into the syringe barrel 14, the check valve 36 directs the fluid-based sample forced out of the fluid port 24 into the output check valve connection 38 and prevents the sample from flowing back out the inlet path. The fluid-based sample flows through the output check valve connection 38 to the chip block 40.

Within the chip block 40, the fluid-based sample is directed from the output connection 38 through microfluidic circuit 56 and into the fluid chamber 76 of the purification chip 48 via the input port 72. The fluid-based sample flows past the plurality of pillars 78 within the fluid chamber 76 to the output port 74. As the fluid-based sample flows past the plurality of pillars 78, one or more analytes within the fluid-based sample are collected on the plurality of pillars 78. The fluid-based sample that reaches the output port 74 is directed from the output port 74 to waste connection 54 via microfluidic circuit 58. The waste connection 54 is preferably coupled to a waste collector, where the collected fluid-based sample is treated as waste. Alternatively, fluid-based sample that reaches the waste connection 54 can be collected to be processed again through the extraction device 10. To perform optical analysis on the one or more analytes collected on the pillars 78, the one or more analytes are prepared for detection using one of the methods previously described To flow an additional one or more solutions through the purification chip 48, the handheld and portable extraction device 10 is used in the same manner described above related to the fluid-based sample to deliver each solution into the purification chip 48. Once the one or more analytes are prepared for detection, the optical analysis system 100 detects and analysis the one or more analytes.

Figure 9:
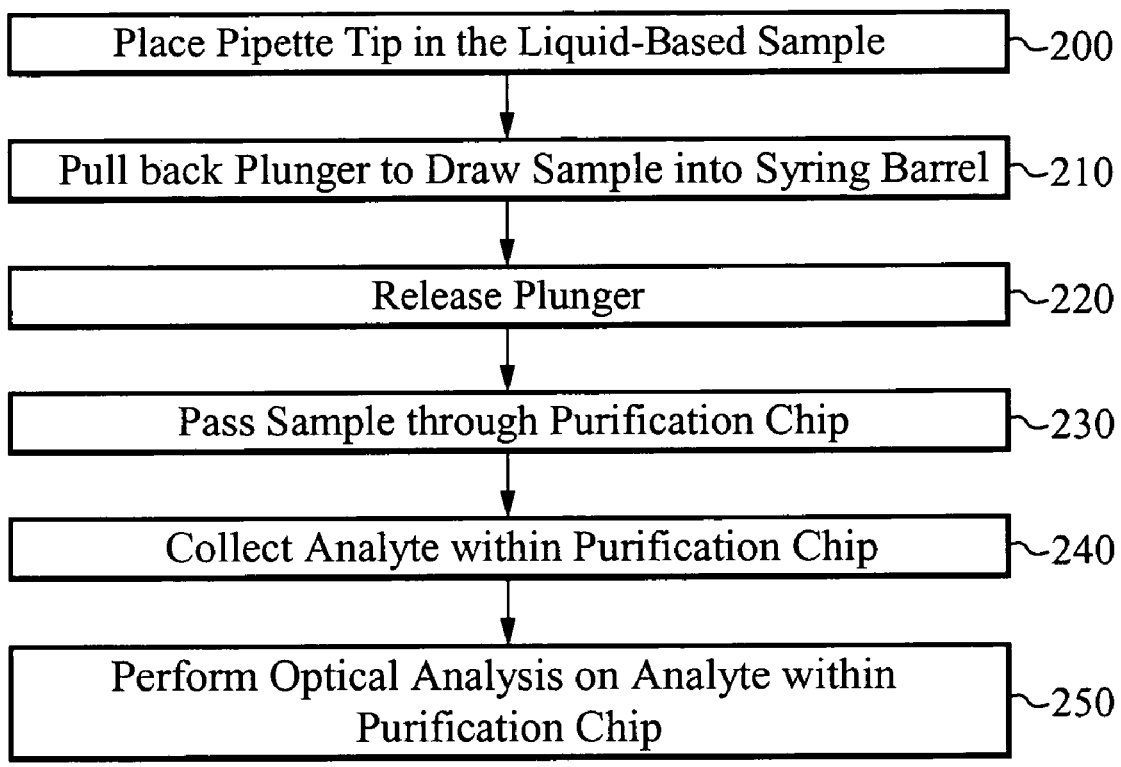
FIG. 9 illustrates a method of operating the handheld and portable extraction device.

Operation of the extraction device 10 is generalized in the method illustrated in FIG. 9. In the step 200, the pipette tip 30 is placed in the fluid-based sample. In the step 210, the plunger 12 is pulled back to draw the fluid-based sample into the syringe barrel 14. In the step 220, the plunger 12 is released. Upon release of the plunger 12, the spring 16 coupled to the plunger 12 exerts a pressure on the fluid-based sample drawn into the syringe barrel 14. In response to the induced pressure, the fluid-based sample is forced out of the syringe barrel 14 and into the purification chip 48. At the step 230, the fluid-based sample passes through the purification chip 48. At the step 240, an analyte, such as nucleic acid, is collected within the purification chip 48 and the remaining fluid-based sample passes through as waste. At the step 250, the one or more analytes are prepared for detection and optical analysis is performed on the one or more analytes while the one or more analytes are bound to the plurality of pillars 78. Steps 200-240 can be repeated multiple times to process larger volumes of fluid.

The extraction device 10 is designed such that the chip block 40 is removable. The threaded nipple 39 screws into the chip block 40, and the chip block 40 is removable by unscrewing the chip block 40 from the threaded nipple 39. Alternatively, the threaded nipple 39 snaps into the chip block 40, and the chip block 40 is removable by pulling the chip block off of the threaded nipple 39. Still alternatively, the threaded nipple 39 is made of a breakable material such that the chip block 40 is removed by breaking in two the threaded nipple 39. Alternatively, any method of removably coupling the chip block 40 to the threaded nipple 39 can be used.

Once the fluid-based sample passes through the purification chip 48, the purification chip 48 can be disconnected from the extraction device 10 to remove any collected analytes from within the purification chip 48.

Although the handheld and portable extraction device 10 has been described in terms of a single iteration of sample extraction while on-site, multiple iterations can be performed. In this case, the fluid-based sample that passes through the purification chip is collected and then drawn back into the extraction device as described above in relation to the first iteration. Any fluid-based sample that passes through the purification chip can be collected and re-drawn into the extraction device any number of iterations. Or, where the fluid-based sample is originally drawn from a sufficiently large source, once the first fluid-based sample passes through the extraction device, another fluid-based sample can be drawn from the source using the same extraction device. This process can be repeated any number of times to draw multiple fluid-based samples from the original source. Such a method is useful in the case where a large sample source exists which may include a diluted nucleic acid.

The handheld and portable extraction device 10 has been described above as comprising separate elements fitted together, such as the pipette tip 30, the filter holder 32, the input connection 36, the check valve 34, the output connection 36, and the syringe barrel 14. The present invention also considers that some or all of the elements comprising the extraction device 10 can be integrated together, such as being form molded.

It is understood that the size of the syringe barrel can be larger or smaller depending on the application. As the size of the syringe barrel changes, so too does the force required to achieve the desired fluid flow rate of the fluid-based sample through the purification chip.

Figure 10:
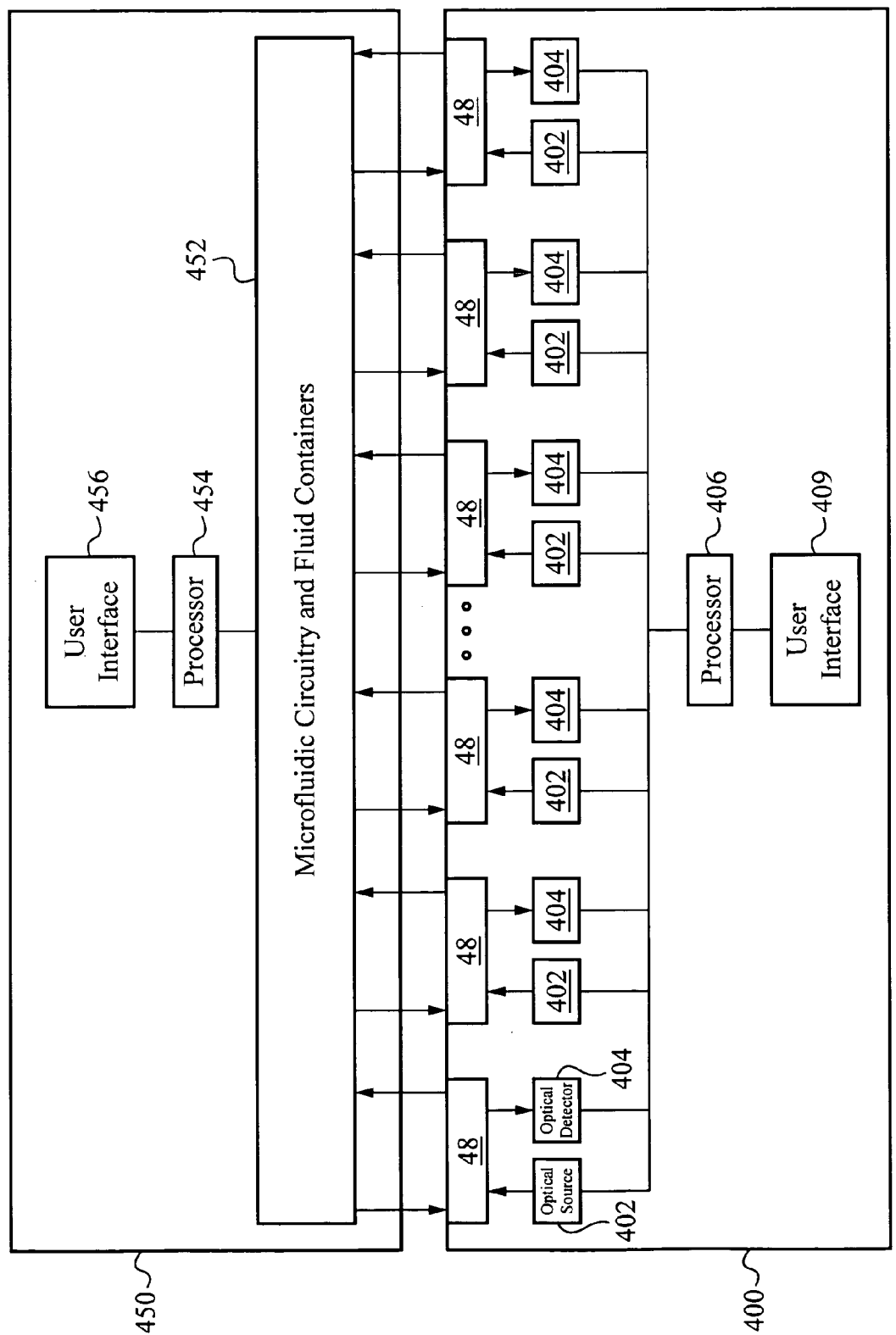
FIG. 10 illustrates a multiple chip system.

FIG. 10 illustrates a multiple chip system in which a plurality of purification chips 48 are mounted within an optical analysis system 400 and coupled to a fluid delivery system 450. The optical analysis system 400 includes multiple chip holders, the bottom of which are optically transparent. Mounted under each chip holder within the optical analysis system 400 is an optical source 402 and an optical detector 404. A purification chip 48 is placed in each chip holder such that the one or more analytes collected within the purification chip 48 are optically accessible by the optical source 402 and the optical detector 404. The optical source 402 directs light into the fluid chamber 76 (FIG. 1) of the purification chip 48. The optical source 402 can be configured to provide any wavelength of light necessary to perform the required optical analysis. The optical source 402 is any conventional light source including, but not limited to, an LED or a laser light provided via fiber optics. The optical detector 404 is any conventional optical detection device capable of detecting light directed from the purification chip 48 in response to the optical source 402. The processor 406 is coupled to each of the optical sources 402 and to each of the optical detectors 404. The processor 406 controls operation of the optical source 402 and optical detector 404, performs analysis of the measurements received from each of the optical detectors 404, and provides results of the analysis to the user interface 409. The user interface 409 preferably includes a keypad for a user to provide instructions to the processor 406 and a display to provide instructions and to display the results of the analysis performed by the processor 406.

The fluid delivery system 450 is aligned to the optical analysis system 400 such that inlet microfluidic circuitry provides fluid to the inlet port 72 (FIG. 1) and outlet microfluidic circuitry receives fluid from the outlet port 74 (FIG. 1) of each of the purification chips 48 mounted within the optical analysis system 400. The fluid delivery system 450 includes microfluidic circuitry and fluid contains 452 that provide microfluidic pathways between any number of fluid containers and the purification chips 48. The fluid containers store various antibodies, enzymes, and other chemistries used to perform the aforementioned process steps, such as the optical analysis, of the extraction and analysis device. A user interface 456 includes a user input and display which enables a user to provide control instructions to a processor 454. The processor 454 functions to control the microfluidic delivery of the various fluids stored in the fluid contains.

In general, each of the purification chips can be derivatized to bind with a different analyte, the same analyte, one or more analytes, or any combination thereof. For example, a first purification chip can be derivatized to bind with protein toxins, such as SEB, a second purification chip to Ricin, and so on. An exemplary application of the multiple chip system is a benchtop instrument used for high-throughput.

In an alternative embodiment, the extraction and analysis device described above is modified such that the optical analysis system is replaced by any conventional detection and analysis system. In this alternative embodiment, the purification chip collects one or more analytes that are detectable by a detecting means other than optical, for example electrical, chemical-luminescence, and electrochemical. Where electrical detection is used, the pillars are coated with an electrically conduction material, such as gold or silver, and the pillar is then derivatized such that binding of a subsequent analyte and/or second antibody generates a measurable electrical current. In another alternative embodiment, the detection and analysis system includes multiple different detection means, each of which can be applied to each purification chip requiring detection and analysis.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of performing a PCR reaction comprising:
   a. providing a PCR apparatus comprising a purification chip including a chamber having a plurality of raised structures, each raised structure is coated with a capture moiety to bind with one or more different nucleic acids, and a thermally controlled device coupled to the plurality of raised structures to thermally control the plurality of raised structures;
   b. providing PCR reagents to the chamber within the purification chip; and
   c. performing a PCR reaction within the purification chip by alternatively raising and lowering a temperature of the plurality of raised structures, thereby alternatively raising and lowering a temperature of one or more substances either attached to the plurality of raised structures or in-solution surrounding the plurality of raised structures.

2. The method of claim 1 further comprising detecting one or more different amplified nucleic acids resulting from the PCR reaction, wherein the one or more different amplified nucleic acids are detected in the chamber.

3. The method of claim 2 wherein detecting the one or more different amplified nucleic acids includes directing light into the chamber and to capture light in response to the directed light.

4. The method of claim 1 wherein detecting the one or more different amplified nucleic acids includes detecting one or more optical characteristics associated with the one or more different amplified nucleic acids.

5. The method of claim 4 wherein detecting the one or more different amplified nucleic acids includes performing one or more of a fluorescence method, a chi-luminescence method, or a time resolved fluorescence method to detect the one or more optical characteristics.

6. The method of claim 1 wherein raising the temperature breaks the binding between the raised structure and the one or more different nucleic acids bound to the raised structure.

7. The method of claim 2 wherein lowering the temperature enables the one or more different nucleic acids to bind to the raised structures.

8. The method of claim 1 wherein the PCR apparatus further comprises one or more solution containers for storing the PCR reagents.

9. The method of claim 8 wherein the PCR apparatus further comprises microfluidic circuitry coupled to the one or more solution containers and the chamber to transport the PCR reagents.

* * * * *